United States Patent
Smith et al.

(10) Patent No.: US 10,575,804 B2
(45) Date of Patent: *Mar. 3, 2020

(54) UPRIGHT X-RAY BREAST IMAGING WITH A CT MODE, MULTIPLE TOMOSYNTHESIS MODES, AND A MAMMOGRAPHY MODE

(71) Applicant: Hologic, Inc., Bedford, MA (US)

(72) Inventors: Andrew P. Smith, Lexington, MA (US); Jay A. Stein, Boston, MA (US); Ken Defreitas, Patterson, NY (US); Ian Shaw, Yorktown Heights, NY (US); Zhenxue Jing, Chadds Ford, PA (US); Loren Niklason, N. Tetonia, ID (US); Baorui Ren, Andover, MA (US); Christopher Ruth, Boxford, MA (US)

(73) Assignee: HOLOGIC, INC., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/144,425

(22) Filed: May 2, 2016

(65) Prior Publication Data

US 2017/0086765 A1  Mar. 30, 2017
US 2017/0325767 A9  Nov. 16, 2017

Related U.S. Application Data

(63) Continuation of application No. 14/330,533, filed on Jul. 14, 2014, now Pat. No. 9,808,214, which is a (Continued)

(51) Int. Cl.
*A61B 6/04* (2006.01)
*A61B 6/00* (2006.01)
(Continued)

(52) U.S. Cl.
CPC .............. *A61B 6/502* (2013.01); *A61B 6/025* (2013.01); *A61B 6/027* (2013.01); *A61B 6/032* (2013.01);
(Continued)

(58) Field of Classification Search
CPC ........ A61L 6/502; A61L 6/5235; A61L 6/482; A61L 6/466; A61L 6/463; A61L 6/4447;
(Continued)

(56) References Cited

U.S. PATENT DOCUMENTS 8,787,522 B2 * 7/2014 Smith .................... A61B 6/025
378/37
9,668,711 B2  6/2017 Smith et al.
(Continued)

FOREIGN PATENT DOCUMENTS

JP  2006-136741  6/2006
JP  2012-157551  8/2012
(Continued)

OTHER PUBLICATIONS

Extended European Search Report issued by the European Patent Office dated Mar. 16, 2017 in connection with European Application No. EP 11831518.
(Continued)

Primary Examiner — Courtney D Thomas
(74) Attorney, Agent, or Firm — Cooper & Dunham LLP

(57) ABSTRACT

A multi-mode system and method for imaging a patient's breast with x-rays in one or more of a CT mode, a narrow-angle tomosynthesis mode, a wide angle tomosynthesis mode, and a mammography mode, using essentially the same equipment, on one or more compressions or immobilizations of the breast.

20 Claims, 7 Drawing Sheets

Related U.S. Application Data continuation of application No. 13/253,728, filed on Oct. 5, 2011, now Pat. No. 8,787,522.

(60) Provisional application No. 61/390,053, filed on Oct. 5, 2010.

(51) Int. Cl.
*A61B 6/02* (2006.01)
*A61B 6/03* (2006.01)

(52) U.S. Cl.
CPC .............. *A61B 6/04* (2013.01); *A61B 6/0414* (2013.01); *A61B 6/405* (2013.01); *A61B 6/4441* (2013.01); *A61B 6/4447* (2013.01); *A61B 6/461* (2013.01); *A61B 6/463* (2013.01); *A61B 6/466* (2013.01); *A61B 6/482* (2013.01); *A61B 6/5235* (2013.01)

(58) Field of Classification Search
CPC ........ A61L 6/025; A61L 6/405; A61L 6/0414; A61L 6/04; A61L 6/032; A61L 6/027; A61L 6/4441
See application file for complete search history.

(56) References Cited

U.S. PATENT DOCUMENTS

| | | | |
|---|---|---|---|
| 9,808,214 B2 | 11/2017 | Smith et al. | |
| 10,098,601 B2* | 10/2018 | Smith | A61B 6/025 |
| 2002/0122533 A1* | 9/2002 | Marie | A61B 6/4441 |
| | | | 378/196 |
| 2003/0194050 A1 | 10/2003 | Eberhard et al. | |
| 2005/0084073 A1 | 4/2005 | Seppi et al. | |
| 2005/0113681 A1 | 5/2005 | DeFreitas et al. | |
| 2007/0223651 A1 | 9/2007 | Wagenaar et al. | |
| 2010/0177866 A1* | 7/2010 | Shibuya | A61B 6/032 |
| | | | 378/20 |
| 2018/0035963 A1* | 2/2018 | Smith | A61B 6/025 |

FOREIGN PATENT DOCUMENTS

| | | |
|---|---|---|
| WO | WO 2012/048000 | 4/2012 |
| WO | WO 2015/054518 | 4/2015 |

OTHER PUBLICATIONS

Aug. 1, 2018 official action in connection with Japanese patent application No. 2016-521343.

* cited by examiner

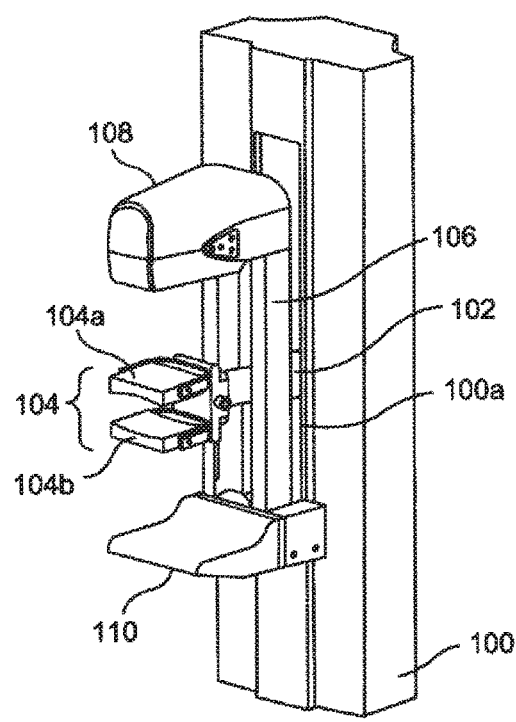
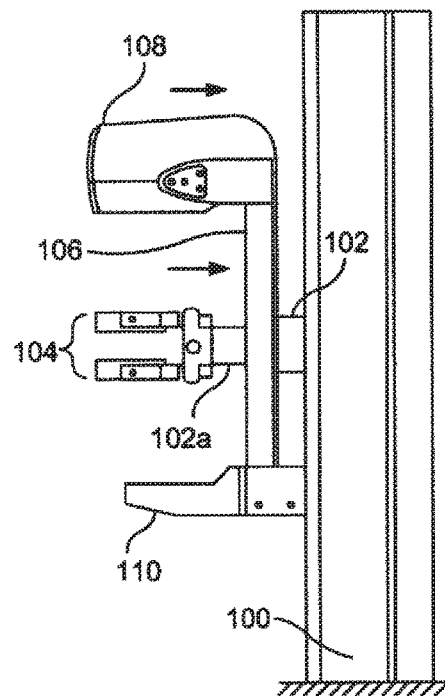
FIG. 1
FIG. 2

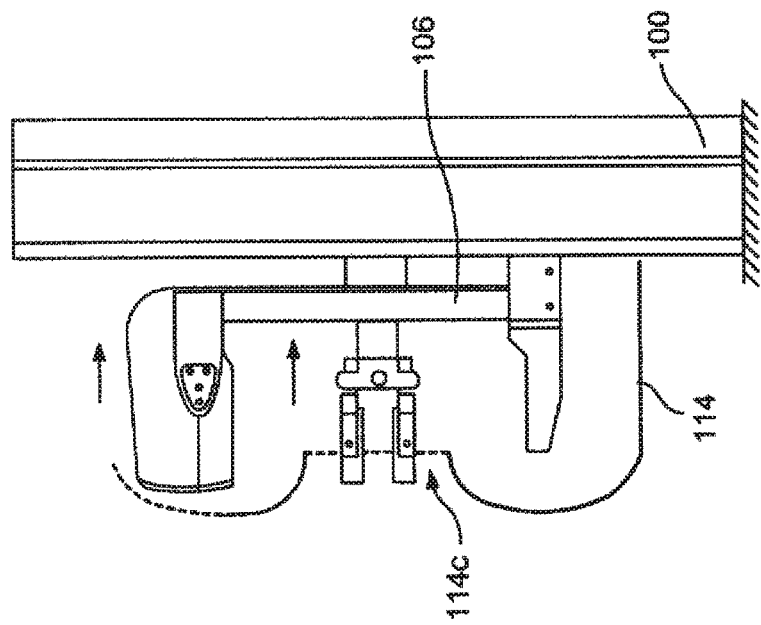
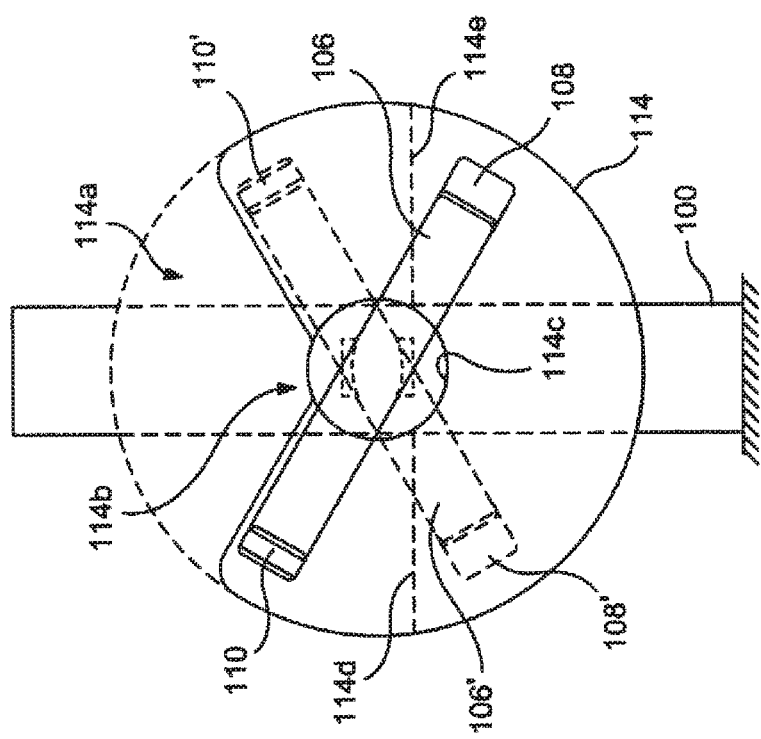

UPRIGHT X-RAY BREAST IMAGING WITH A CT MODE, MULTIPLE TOMOSYNTHESIS MODES, AND A MAMMOGRAPHY MODE

CROSS-REFERENCE TO RELATED APPLICATIONS

This application is a continuation application of U.S. application Ser. No. 14/330,533, filed on Jul. 14, 2014, which is a continuation application of U.S. application Ser. No. 13/253,728, filed on Oct. 5, 2011, which claims the benefit of U.S. Provisional Ser. No. 61/390,053, filed on Oct. 5, 2010. These applications are hereby incorporated by reference herein in their entireties.

FIELD

This patent specification pertains to x-ray imaging of the breast and, more specifically, to a system for selectively imaging a breast of an upright patient in one or more of a CT mode, one or more tomosynthesis modes (e.g., narrow angle breast tomosynthesis and wide angle breast tomosynthesis), and a mammography mode. The system preferably is integrated so that the equipment can be used for any one or more of these imaging modes. The patient can be standing, as is typical for mammography and tomosynthesis, rather than lying down as in conventional CT. In the CT mode, the imaging x-ray beam passes only through the breast, not through the patient's torso as when a conventional CT system is used to image the breast.

BACKGROUND

X-ray mammography is the established screening modality for breast cancer and other lesions, and also has been relied on for diagnostic and other purposes. Historically, the breast image has been recorded on x-ray film but more recently digital x-ray image receptors have come into wide use, as in the mammography system available under the trade name Selenia from the common assignee hereof, Hologic Inc. of Bedford, Mass., and from its division Lorad Corporation of Danbury, Conn. In mammography, typically a pyramid-shaped x-ray beam passes through the compressed breast and forms a two-dimensional projection image, namely, a mammogram identified herein as images M. Any one of a number of orientations can be used, such as CC (cranial-caudal) or MLO (mediolateral-oblique).

More recently, breast x-ray tomosynthesis has come into use. The common assignee has installed breast tomosynthesis systems for clinical use in this country and has sold such systems overseas. The technology typically involves taking two-dimensional (2D) projection images, identified herein as images Tp, of the immobilized breast at each of a number of angles of the x-ray beam relative to the breast. The resulting x-ray measurements are computer-processed to reconstruct images, identified herein as images Tr, of breast slices that, typically are in planes transverse to the x-ray beam axis, such as parallel to the image plane of a mammogram of the same breast, but can be at any other orientation and can represent breast slices of selected thicknesses. The range of angles is substantially less than in conventional CT (computerized tomography), i.e. substantially less than 180° plus a fan angle, e.g., a range of ±15°.

An example of a breast x-ray tomosynthesis system is the common assignee's system available under the trade name Selenia Dimensions that is sold overseas and has been installed for clinical testing in this country and includes both a tomosynthesis mode of operation and a mammogram mode of operation. See also U.S. Pat. No. 7,123,684 and U.S. patent application publications 2005/0113681 A1 and 2009/0003519 A1, U.S. Pat. Nos. 4,496,557, 5,051,904, 5,359,637, 6,289,235, 6,375,352, 6,645,520, 6,647,092, 6,882,700, 6,970,531, 6,940,943 7,356,113, 7,656,994, published U.S. Patent Applications Nos. 2004/0066904 and 2007/0263765, and Digital Clinical Reports, Tomosynthesis (GE Brochure 98-5493, November 1998). How to reconstruct tomosynthesis images is discussed in DO Grant, "Tomosynthesis: a three-dimensional imaging technique", IEEE Trans. Biomed. Engineering, Vol BME-19, #1, (January 1972), pp 20-28. See, also, U.S. Provisional Application No. 60/628,516, filed Nov. 15, 2004, and entitled "Matching geometry generation and display of mammograms and tomosynthesis images," and a system announced under the name Giotto Image 3D by a I.M.S. Internazionale Medico Scintifica of Bologna, Italy. Mammography and tomography systems can also be used in interventional procedures, such as biopsy, by adding a biopsy station (for example, the system available from the common assignee under the trade name StereoLoc II Upright Stereotactic Breast Biopsy System). The patents, applications, brochures, and article cited above, as well as those cited below, are hereby incorporated by reference in this patent specification as though fully set forth herein.

X-ray breast imaging systems that can selectively take tomosynthesis projection images and conventional mammograms, such as the system available under the trade name Selenia Dimensions system, are known. They include an x-ray source and an x-ray imaging receptor that can be held in a fixed relationship to each other and moved as a unit to take conventional mammograms M, and can be decoupled from each other so that at least one can move relative to the other and to the patient's breast to take tomosynthesis projection images Tp. See also commonly assigned U.S. Pat. No. 7,583,786.

CT technology has not been widely used for x-ray imaging of the breast. In conventional CT, the patient is lying down on a gurney or platform while the x-ray source and detectors rotate about the patient. The x-ray measurements are reconstructed into images, referred herein as images CTr, of typically planar slices of the patient. The imaging planes that intersect the breast also intersect the torso and so the patient's body is unnecessarily subjected to x-radiation when only an x-ray image of the breast is of interest. In addition, the use of conventional CT for breast images can be unduly expensive. There have been proposals for CT systems that would image only the breast, without imaging the torso as well, but they require the patient to be in a prone position and also have not found wide use. See, for example, U.S. Pat. No. 3,973,126, proposing to suspend the breast of a prone patient into an opening around which an x-ray source and an x-ray detector would rotate in a horizontal plane. See also U.S. Pat. No. 6,987,831, proposing a very similar arrangement that uses more modern components. In addition, published U.S. patent publication 2010/0080343 A1 proposes a breast CT system in which the patient's breast protrudes through an opening in a vertical wall to thereby extend to the other side of the wall, where a gantry rotates an x-ray source and detector in a spiral scan motion or successive slice scan motion to image the protruding portions of the breast.

It can be desirable for a number of reasons to assess different types of x-ray images of a patient's breast. For example, over decades of reading conventional mammograms M, medical professionals have developed valuable interpretation expertise. Mammograms M may offer good visualization of micro calcifications, and may offer higher spatial resolution compared with tomosynthesis images Tp or Tr. Tomosynthesis images Tr may have different desirable characteristics—e.g., they may offer better visualization of structures that can be obscured by overlying or underlying tissue in a conventional mammogram M. CT images CTr can offer other benefits, such as the ability to obtain attenuation values for specific tissue inside the breast and to generate a three-dimensional image of volume elements (voxels) in the breast that is generally free of geometric distortions and thus can be conveniently re-processed into images of breast slices at any orientation and with any thickness. However, no system is known to the inventors herein that would make it possible to select which one or more of these three types of breast images to take with a single system, without moving the patient from one imaging system to another and perhaps from one medical facility to another.

It also can be desirable to co-register breast images taken with different x-ray modalities, e.g., so that the same real or suspected lesion can be viewed and assessed in the images from two or more modalities, as each modality may contribute different information about the lesion. While some aspects of co-registration have been provided for tomosynthesis images Tr and Tp and mammograms M (see, e.g., commonly owned U.S. Pat. Nos. 7,577,282 and 7,616,909), no co-registration is known for x-ray CT breast images, especially if taken from an upright patent, with Tr, Tp, and M x-ray images of the breast.

SUMMARY

This patent specification describe-s a multi-mode system that includes an x-ray CT system taking CT breast x-ray images CTr of an upright patient positioned with respect to the system in a way similar to a patient's position relative to a conventional mammography system, while providing protection from moving assemblies using a design uniquely suited to x-ray CT scanning of the breast. The same system can be configured to selectively take not CT but tomosynthesis images Tp and Tr in one of at least two tomosynthesis modes, such as a wide angle mode and a narrow angle mode. And, the same system can be configured to selectively take mammograms M that are essentially the same as, or are similar in appearance to, conventional mammograms taken with a mammography system. Thus, the same system can operate in any one, or any two or more, of several modes for breast imaging: a CT mode, plural tomosynthesis modes including for example a wide angle tomosynthesis mode and a narrow angle tomosynthesis mode, and a mammography mode. Breast images of the patent can be taken in a single one of these modes, or in two or more of these modes, while the patient's breast remains immobilized, or in different immobilizations of the breast during the same study, or at different times. Preferably, the imaging x-ray receptor is a two-dimensional receptor that can image the entire breast in the mammography mode, so that preferably the same receptor can be used in the CT scan mode in a single rotational motion, thus avoiding the need to scan multiple times around the breast in order to acquire x-ray measurements for multiple slices of the breast.

BRIEF DESCRIPTION OF THE DRAWING

FIG. 1 is a perspective view of a portion of an upright breast x-ray imaging system illustrated as operating in a CT mode but also configured to selectively operate in at least two tomosynthesis modes and a mammography mode.

FIG. 2 is a side elevation of the system of FIG. 1.

FIG. 3 is a front elevation illustrating a patient shield for a system similar to that seen in FIGS. 1 and 2.

FIG. 4 is a side elevation that is the same as FIG. 2 but illustrates a patient shield.

DETAILED DESCRIPTION OF PREFERRED EMBODIMENTS

Figures 5, 6:
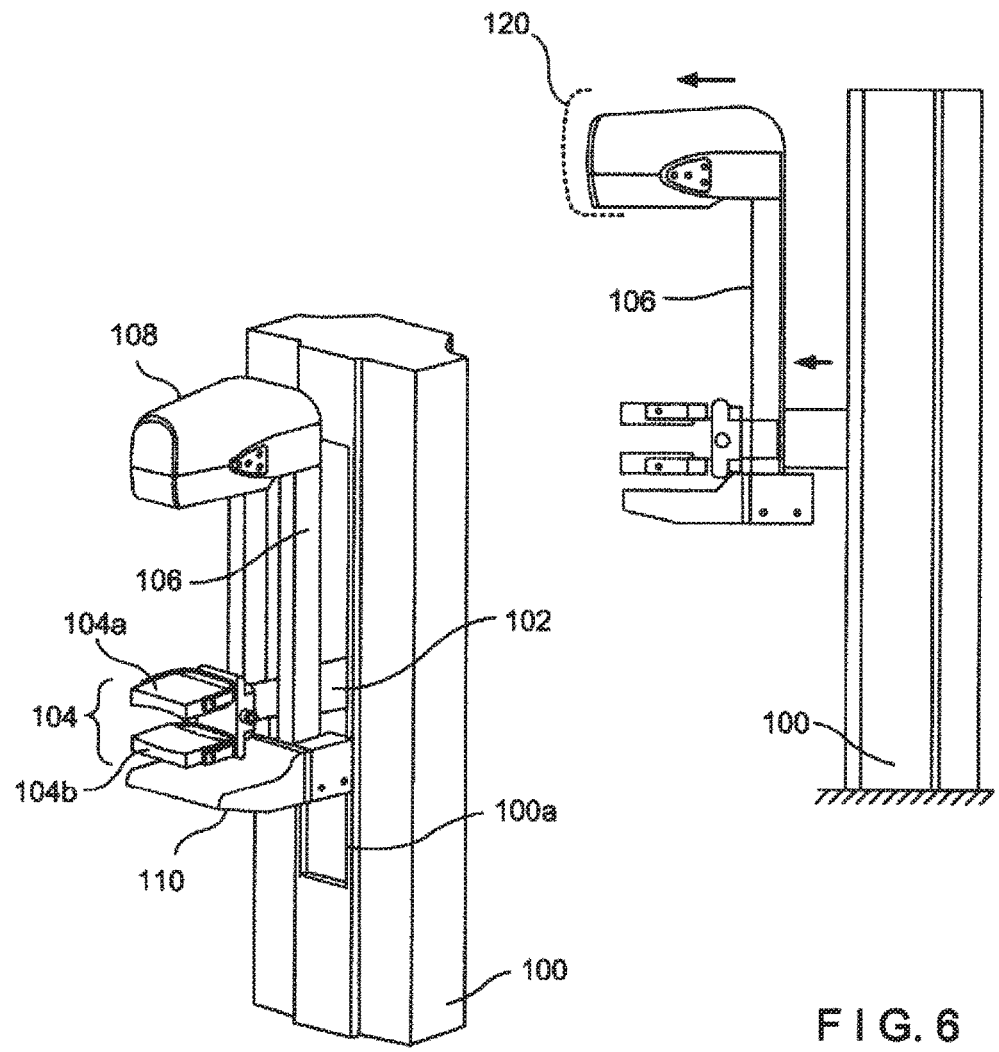
FIGS. 5 and 6 are similar to FIGS. 1 and 2, respectively, but illustrate the system as used in a tomosynthesis mode or a mammography mode and shows a gantry that is spaced further from a support column than in FIGS. 2 and 4.

In describing examples and preferred embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

FIGS. 1 and 2 illustrate portions of a non-limiting example of a multi-mode breast x-ray imaging system operable in a CT mode but also configured to selectively operate in a tomosynthesis mode including a wide angle tomosynthesis mode and a narrow angle tomosynthesis mode, and in a mammography mode. For clarity of illustration, a patient shield for use in the CT mode is omitted from FIGS. 1 and 2 but examples are illustrated in FIGS. 3, 4, 10 and 11. A support column 100 is secured to a floor and houses a motorized mechanism for raising and lowering a horizontally extending axle 102, which protrudes through an opening 100a in column 100, and for rotating axle 102 about its central axis. Axle 102 in turn supports a coaxial axle 102a that can rotate with or independently of axle 102. Axle 102 supports a breast immobilization unit comprising an upper plate 104a and a lower plate 104b such that each plate can move up and down along the long dimension of support 100 together with axles 102 and 102a, at least one of the plates can move toward the other, and unit 104 can rotate about the common central axis of axles 102 and 102a. In addition, axle 102 supports a gantry 106 for two types of motorized movement: rotation about the central axis of axle 102, and motion relative to axle 102 along the length of gantry 106. Gantry 106 carries at one end an x-ray source such as a shrouded x-ray tube generally indicated at 108, and at the other end a receptor housing 110 enclosing an imaging x-ray receptor 112 (not visible in FIGS. 1 and 2 but illustrated in FIG. 7).

When operating in a CT mode, the system of FIGS. 1 and 2 immobilizes a patient's breast between plates 104a and 104b. To this end, unit 104 is raised or lowered together with axle 102 to the height of the breast while the patient is upright, e.g., standing or sitting. The patient leans toward unit 104 from the left side of the system as seen in FIG. 2, and a health professional, typically an x-ray technician, adjusts the breast between plates 104a and 104b while pulling tissue to the right in FIG. 2 and moving at least one of plates 104a and 104b toward the other to immobilize the breast and keep it in place, preferably with as much as practicable of the breast tissue being inside unit 104. In the course of taking x-ray measurements representing CT projection x-ray images CT[, from which to reconstruct images CTr of respective breast slices, gantry 106 rotates about the central axis of axle 102 while the breast remains immobilized in unit 104. Preferably, imaging receptor 112 inside housing 110 remains fixed relative to x-ray tube 108 during the rotation of gantry 106. A pyramid shaped beam of x-rays from tube 108 traverses the breast immobilized in unit 104 and impinges on imaging receptor 112, which in response generates a respective two-dimensional array of pixel values related to the amount of x-ray energy received for each increment of rotation at respective pixel positions in an imaging plane of the receptor. These arrays of pixel values for images CTp are delivered to and processed by a computer system (not shown in FIGS. 1 and 2 but illustrated in FIG. 9) to reconstruct slice images CTr or the breast. Gantry 106 may be configured for motorized movement toward column 100, to facilitate the x-ray technician's access to the patient's breast for positioning the breast in unit 104, and away from column 100 to ensure that x-ray tube 108 and imaging receptor 112 inside housing 110 can image the appropriate breast tissue. Alternatively, gantry 106 can maintain a fixed distance from column 100, to the left of the position seen in FIG. 2, so that the imaging x-ray beam can pass through as much as practical of the breast immobilized in unit 104, in which case there would be no need for a mechanism to vary that distance.

A unique challenge arises because of the upright position of the patient and the rotation of x-ray tube 108 and receptor housing 110 through a large angle in the CT mode of operation. As known, CT scanning typically involves a rotation of the source and receptor through an angle of 180° plus the angle subtended by the imaging x-ray beam, and preferably a rotation through a greater angle, e.g., 360°. However, if the rotation includes the 0° position of x-ray source 108 as seen in FIGS. 1 and 2, the patient's head may be too close to x-ray source 108. Collision of rotating assemblies with the patient, and concern with such collision, can be avoided by the use of a shield separating the patient from assemblies rotating even the full 360, as discussed below in this patent specification, although depending on the design of the shield and the rotating assemblies in particular embodiments this may require the patient to arch her body such that both her head and legs are away from the system, to the left as seen in FIG. 2. An alternative, also discussed below, is to exclude from the rotation a sector or segment around the position of x-ray source 108 seen in FIGS. 1 and 2. As a non-limiting example, if the position of x-ray tube 108 seen in FIGS. 1 and 2 is designated the 0° position, then the rotation for CT imaging excludes positions of x-ray source 108 in the 90° sector or segment between 45° and 315°, or in the 120° sector or segment between 60° and 300°, or in some other sector or segment that is sufficient to clear the patient's head position while taking x-ray CT data over a sufficient angle of rotation for the reconstruction of high quality CTr images. While the rotation of x-ray tube 108 and receptor housing 110 still has to clear the lower part of the patient's body, it is generally easier for a patient to keep the lower part of her body away from the rotating components, to the left as seen in FIG. 2 (and preferably behind a shield), than to arch back her head and shoulders.

An example of such a shield is illustrated, in FIGS. 3 and 4. FIG. 4 is a side elevation that is otherwise the same as FIG. 2 but additionally illustrates a patient shield 114 having a central opening 114c. Shield 114 may be completely circular in front elevation, as illustrated by the circle that includes an arc in broken line in FIG. 3, in front elevation. In that case, gantry 106 can rotate through a complete circle in the CT mode. As an alternative, shield 114 can leave open a sector or segment 114a illustrated in FIG. 3 as the area below the broken line arc and between the solids line of shield 114. In that case, gantry 106 can rotate in the CT mode only through an angle that is less than 360°, but the patient can have space for her head and perhaps a shoulder and an arm in the V-shaped cutout 114b of shield 114, for a more comfortable body posture. Specifically, as illustrated in FIG. 3, gantry 106 can rotate only within the portion of shield 114 that is outside V-shaped cutout 114b. One of the possible positions of gantry 106 and tube 108 and receptor housing 110 is shown in solid lines. Mother possible position is shown in broken lines, and designated as gantry 106', carrying x-ray source 108' and receptor housing 110'. FIG. 4 illustrates a possible shape of shield 114 in side elevation. Shield 114 bulges away from central opening 114c in a direction away from column 100, to allow the patient's breast to reach and become immobilized in unit 104 while the patient's body is separated by shield 114 from the rotating components, namely gantry 106 and x-ray source 108 and receptor housing 110. Opening 114c may be made larger, and may be shaped differently from the illustration in FIGS. 3 and 4 (which are not to scale) to facilitate access by the x-ray technician to the patient's breast as the breast is being immobilized. Portions of shield 114 may be removable or hinged to further facilitate access. For example, one or both of the portions of shield 114 above broken lines 114d and 114e may be removable or hinged such that they can be moved out of the way while the technician is positioning and immobilizing the patient's breast, and put back to protect the patient before scanning in the CT mode starts. Patient shield can be mounted on column 100 and/or the floor. In the example of FIGS. 3 and 4, the rotating gantry 106 can be moved to the left or to the right so that it is closer to or further away from the patient, i.e., from one to the other of the position seen in FIG. 4 and the position seen is FIG. 6. Thus, for CT imaging of the breast using the example of FIG. 3, rotating gantry 106 would be spaced away from column 100, to the position relative to column 100 illustrated in FIG. 6 while actually imaging the patient's breast only while the receptor housing 110 is outside the cutout 114b. Thus, the patient can lean forward, partly into cutout 114b so that more of the beast being imaged, and possibly surrounding tissue, can come into the x-ray imaging field.

Another challenge in upright breast CT is how to immobilize the breast. In some cases, for various reasons little or no compression of the breast may be desirable. In other cases, it may be desirable to compress or otherwise act on the breast, for example so that breast tissue can be pulled away from patient's chest wall and securely retained in unit 104 for imaging. To this end, and to generally increase patient comfort, at least one, and preferably both, of plates 104a and 104b have concave facing surfaces as seen in FIG. 6 designed to hold the breast for CT imaging while keeping it close to round and thus with close to equal path lengths of x-rays at least within individual CT slices. Plates 104a and 104b may be removably secured so that different sets of plates can be used to accommodate differently sized or shaped breasts. Different degrees of breast compression can be used as selected by a health professional operating the system of FIGS. 1-4. In still other cases, it may be desirable to use other means to pull breast and chest wall tissue into the x-ray imaging field, such as providing a cup-shaped or funnel-shaped enclosure into which the breast and possibly surrounding tissue is pulled by vacuum, adhesion or other means, illustrated in block diagram form in FIG. 9.

Yet another challenge in upright breast. CT is that the path lengths of x-rays through the breast may differ depending on the part of the breast they traverse. For example, the path lengths through breast portions at or near the nipple may be much shorter than those near the chest wall. When operating in the CT mode, the x-ray technician can shape the patient's breast as it is being immobilized in unit 104 using an x-ray transparent pillow or similar items to make the breast cross-section nearly uniform by pushing the nipple end toward the chest wall and securing the so-shaped breast in unit 104, to thus nearly equalize the x-ray path lengths through the breast. As an alternative that does not involve so shaping the immobilized breast, a shaped x-ray filter can be used in the housing of x-ray tube 108 to shape the x-ray energy distribution of the imaging x-ray beam so that beam hardness increases in the direction from the nipple toward the chest wall. As yet another approach, x-ray path lengths can be equalized or at least made more uniform by a suitably shaped x-ray attenuating material arranged around the breast, in the path of the x-ray beam from the x-ray source.

Use of the system in a tomosynthesis mode is illustrated in FIGS. 5 and 6, which are otherwise the same as FIGS. 1 and 2 respectively, except that gantry 106 is in a different position relative to breast immobilization unit 104 and axle 102 and column 100, and no shield 114 is shown. In particular, x-ray source 108 is further from unit 104 and column 100, and receptor housing 110 is closer to unit 104. In the tomosynthesis mode, the patient's breast also is immobilized between plates 104a and 104b, which remain in place during imaging. In one example, x-ray tube 108 and receptor housing 110 may undergo a rotation about the immobilized breast that is similar to that in the CT mode operation but is through a smaller angle. A respective two-dimensional projection image Tp taken for each increment of rotation while x-ray tube 108 and imaging receptor 112 inside housing 110 rotate as a unit, fixed with respect to each other, as in the CT mode or as illustrated in principle in commonly assigned U.S. Pat. No. 7,123,684, incorporated by reference. Alternatively, the motions of x-ray tube 108 and receptor 112 relative to the immobilized breast can be as in said system offered under the trade name Selenia Dimensions of the common assignee, certain aspect of which are described in commonly owned U.S. Pat. No. 7,616,801, which is hereby incorporated by reference. In this alternative case, x-ray tube rotates about the central axis of axle 102, but receptor housing 110 remains in place while imaging receptor 112 rotates or pivots inside housing 110 about an axis that typically passes through the image plane of the receptor, is parallel to the central axis of axle 102, and bisects imaging receptor 112. The rotation or pivoting of receptor 112 typically is through a smaller angle than the rotation angle of x-ray tube 108, calculated so that a normal to the imaging plane of receptor 112 can continue pointing at or close to the focal spot in x-ray tube 108 from which the imaging x-ray beam is emitted, and so that the beam continues to illuminate all or most of the imaging surface of receptor 112. In one example of tomosynthesis mode operation, x-ray tube 108 rotates through an arc of about ±15° while imaging receptor rotates or pivots through about ±5° about the horizontal axis that bisects its imaging surface. During this motion, plural projection images Tp are taken, such as 20 or 21 images, at regular increments of rotation angle. The central angle of the ±15° arc of x-ray source 108 rotation can be the 0° angle, i.e., the position of the x-ray source 108 seen in FIGS. 5 and 6, or some other angle, e.g., the angle for the x-ray source position typical for MLO imaging in conventional mammography. In the tomosynthesis mode, the breast may be immobilized in unit 104 but, alternatively, lower plate 104b may be removed so that the breast is supported between the upper surface of receptor housing 110 and upper plate 104a, in a manner analogous to the way the breast is immobilized in said system offered under the trade name Selenia. In the tomosynthesis mode, greater degree of breast compression can be used under operator control than in the CT mode. The same concave plates 104a and 104b can be used, or generally flat plates can be substituted, or a single compression paddle can be used while the breast is supported by the upper surface of receptor housing 110, as used in said system offered under the Selenia trade name.

When operating in a tomosynthesis mode, the system of FIGS. 5 and 6 provides multiple choices of that mode, selectable by an operator, for example a narrow angle mode and a wide angle mode. In the narrow angle tomosynthesis mode, x-ray source 108 rotates around unit 104 and the patient's breast immobilized therein through an angle such as ±15°, while in the wide angle tomosynthesis mode x-ray tube 108 rotates through an angle such as in the range of about ±15° to ±60°. The wide angle mode may involve taking the same number of projection images Tp as the narrow angle mode, or a greater number. As a non-limiting example, if the narrow angle mode involves taking a total or 20 or 21 tomosynthesis projection images Tp as x-ray source 108 moves through its arc around the breast, the wide angle mode may involve taking the same number of images Tp or a greater number, such as 40 or 60 or some other number, typically at regular angular increments. The examples of angles of rotation of x-ray source 108 are not limiting. The important point is to provide multiple modes of tomosynthesis operations, where one mode involves x-ray source rotation through a greater angle around the breast than another tomosynthesis mode.

Figure 7:
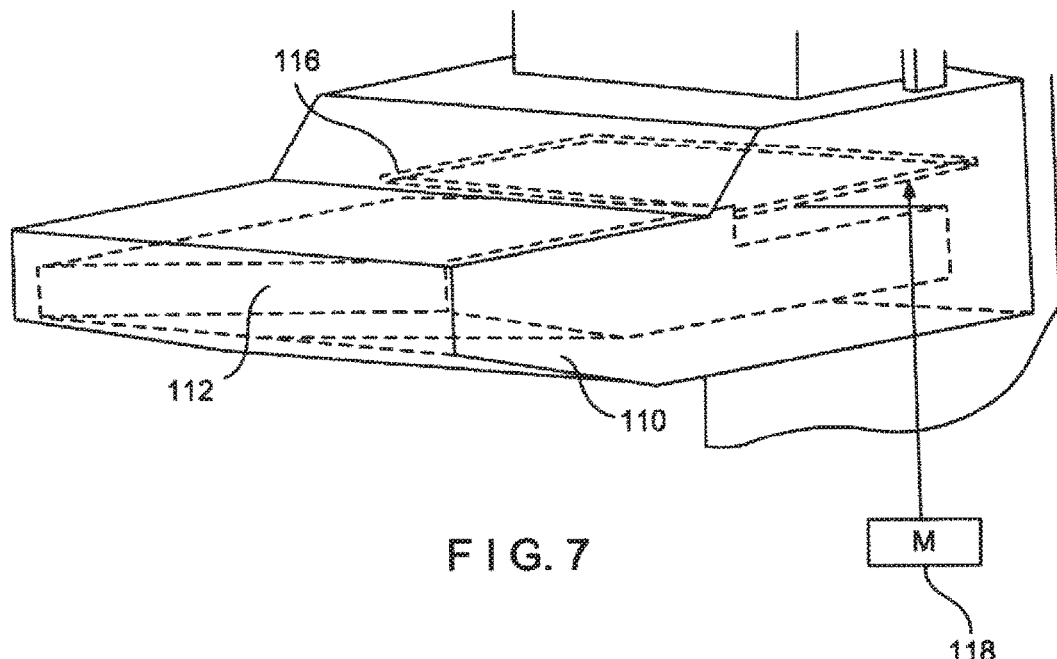
FIG. 7 is a perspective view illustrating an imaging receptor that can pivot inside a receptor housing.

FIG. 7 illustrates imaging receptor 112 inside receptor housing 110. Receptor 112 can be in a fixed position relative to housing 110, with an imaging surface parallel to the upper surface of housing 110, or it can rotate or pivot relative to housing 110 as described above. FIG. 7 illustrates receptor 112 in one extreme of its rotation or pivoting. The other extreme is when its left side (as viewed in FIG. 7) is all the way up against or close to the upper wall of housing 110 and its right side is all the way down. In addition, FIG. 7 illustrates an anti-scatter grid 116 that can be moved out of the x-ray imaging beam, to the position in which it is seen in FIG. 7, or forward so that it overlies the imaging surface of receptor 112, by a grid motor control 118 under commands by the operator or by a computer operating the x-ray imaging system. Typically, grid 116 is out of the imaging beam when receptor 112 is rotating or pivoting inside housing 110 in the course of an x-ray study, and is in the beam if receptor 112 remains in a fixed position in housing 110 during x-ray exposure of the breast. For use in each of the modes described above, imaging receptor 112 can be the two-dimensional, Selenium-based, flat panel, digital detector available from the common assignee and currently used in said system offered under the Selenia trade name. To accommodate the refresh rate of a particular imaging receptor, the timing of taking successive projection images in the CT mode and the tomosynthesis mode can be adjusted accordingly. Imaging receptors that can take successive projection images at a faster rate can be used if desirable. As another alternative, an imaging receptor that cannot image the entire breast at the same time can be used by scanning the receptor relative to the breast to cover the entire breast in one or more sweeps.

In the tomosynthesis modes, a different patient shield can be used to protect the patient, and/or a different trajectory for tube 108 can be used, such as disclosed in commonly assigned U.S. Pat. No. 7,245,694, hereby incorporated by reference. Such a patient shield is schematically illustrated as item 120 in FIG. 6.

When operating in the mammography mode M, the system of FIGS. 5 and 6 maintains imaging receptor 112 inside housing 110 fixed relative to both x-ray source 108 and breast immobilized in unit 104. For taking a CC mammogram Mp, the source can be in the position seen in FIGS. 5 and 6. To take an MLO mammogram Mp, the patient's breast is released from unit 104, gantry 106 rotates about the central axis of axle 102 as a unit, together with unit 104, and the patient's breast is again immobilized in unit 104, in a manner analogous to that used in conventional mammography and with said system offered under the Selenia trade name.

Alternatively, as in the tomosynthesis mode of the system, lower plate 104b can be removed and the breast can be immobilized between the upper surface of receptor housing 110 and upper plate 104a. Typically, the x-ray dose to the patent for taking a mammogram Mp is significantly higher than for taking any one of the tomosynthesis projection images Tp. For example, the dose for one mammogram Mp is the same or comparable to the total dose for all the images Tp taken in one sweep of x-ray source 108 through its arc. As in the tomosynthesis mode, the same concave plates 104a and 104b can be used, or generally flat plates can be substituted, of the type used in said system offered under the Selenia trade name, and the upper surface of housing 110 can substitute for lower plate 104b.

Figure 8:
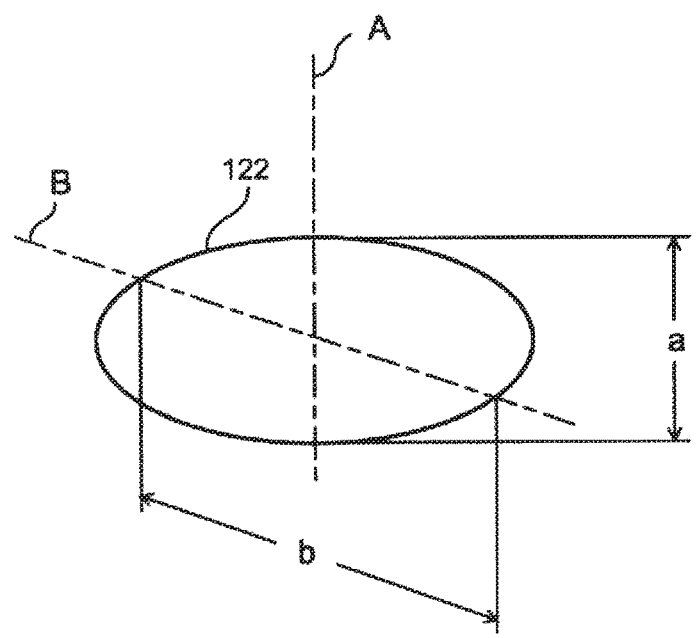
FIG. 8 is a schematic illustration of different path lengths of x-rays through a compressed breast of a patient.

In some or all of the modes, the coronal cross-section of the breast immobilized in unit 104 can be approximately elliptical, as illustrated for breast 122 in FIG. 8, such that the width of the immobilized or compressed breast 122 is significantly more than its thickness. In that case, as seen in FIG. 8, the path length "a" along line A through breast 122 is shorter than path length "b" along line B for x-rays within the imaging beam. To accommodate this situation, it can be desirable to vary the spectrum of the x-rays with angle of the imaging beam relative to the breast. For example, softer x-rays can be used for path "a" than for path "b" in order to improve the x-ray image. To this end, the system when used in the CT mode or in the tomosynthesis modes, and with a breast 122 immobilized to a cross-section that is significantly wider that thick, can be operated under computer control to vary the x-ray beam hardness accordingly, for example by varying the voltage (kV) driving x-ray tube 108. It can be important for a health professional to view concurrently images of a patient's breast or breasts taken with different x-ray modalities. The system disclosed in this patent specification provides that opportunity as it can produce CT images CTr, tomosynthesis images Tp and Tr, and mammograms M.

Figure 9:
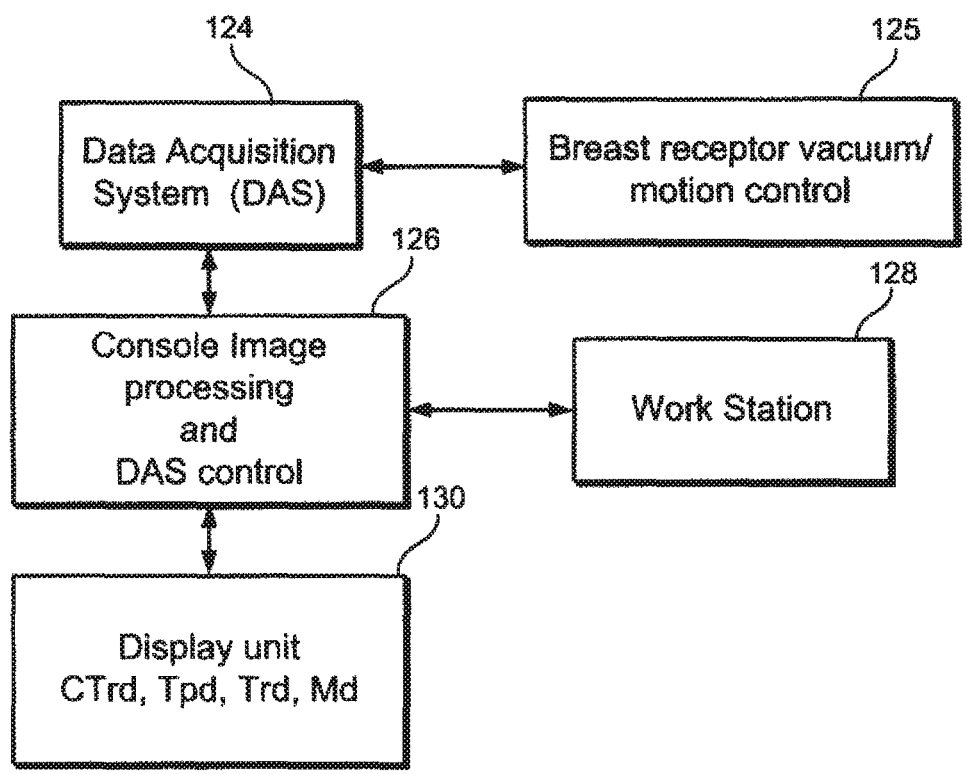
FIG. 9 is a block diagram illustrating an integrated x-ray system.

As illustrated in FIG. 9, the x-ray measurements that are obtained with a data acquisition system 124 that includes x-ray source 108 and imaging receptor 112 operating as described above are provided to a console 126 that includes an image processing unit configured to computer-process the x-ray measurements (which can be in the form of projection images CTp, Tp and Mp) into image data for respective display images CTrd, Trd and Md for viewing, and for controlling data acquisition system 124 to operate as described above. For clarity and conciseness, conventional elements such as power supplies, operator controls and safety devices, are not illustrated. For tomosynthesis images and mammograms, the operation of console 126 can be similar or identical to that used in said system offered under the Selenia Dimensions trade name, or as discussed in said references cited above. For CTr images, the computer processing can operate as discussed in said U.S. Pat. No. 6,987,831. For mammograms, the processing can be as in said system offered uncle the Selenia trade name. The images resulting from the processing in console 126 can be provided to a workstation 128, which can be the workstation offered under the trade name SecurView by the common assignee, and/or to a display unit 130 that includes one or more computer display screens to show, at the same time, two or more of the breast images. For example, display unit 130 can show at the same time, a CTrd image together with a Tpd image and/or a Trd image, and/or an Mpd image. Any one of these types of images can be shown as a single image, as two or more images, or in cine mode. For example, the Trd images can be shown in cine mode changing from an image of one breast slice to and image of another slice. The images displayed at the same time can be co-registered such that the selection of an anatomical feature in one of the concurrently displayed images automatically identifies a matching anatomical feature in at least another one of the concurrently displayed images. If it is desired to immobilize and position the breast for imaging using a device different from unit 104, data acquisition system 124 can include instead a device such as a cup-shaped or funnel-shaped breast receptor 104' (FIG. 10), into which the breast and possibly surrounding tissue can be pulled by means such as vacuum or adhesives, and such device can be controlled by control 125 illustrated in FIG. 9. The cup or funnel would be in place of unit 104, in the imaging beam from x-ray source 108.

Figure 10:
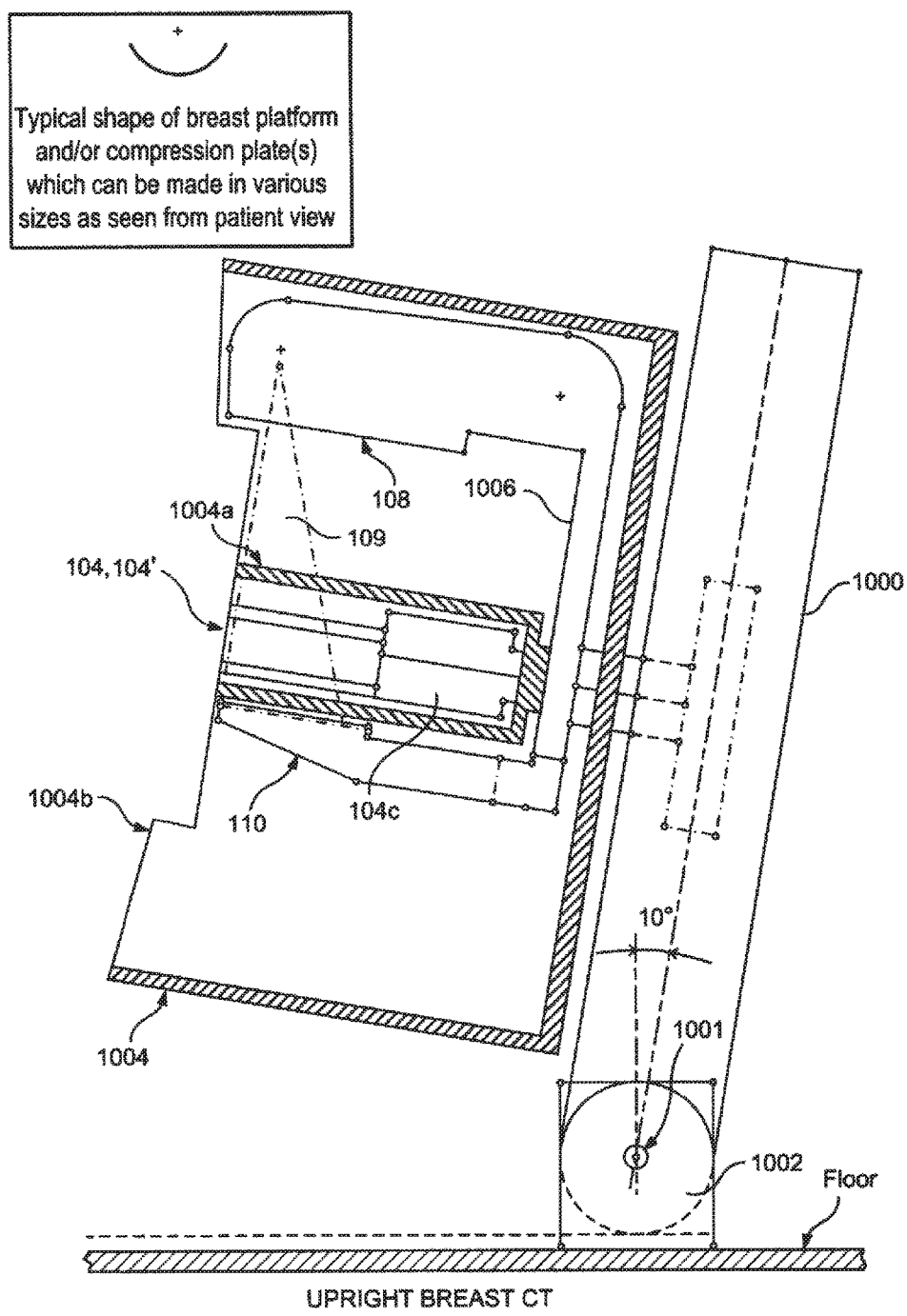
FIGS. 10 and 11 illustrate portions of an alternative embodiment that may improve system operation and patient comfort.

FIG. 10 illustrates another embodiment, where a column 1000 pivots from the vertical about a pivot axis 1001 of a pivoting support 1002, for example over a 10° angle as illustrated, so the patient can lean forward against shield 1004. A rotating C-arm 1006 can carry an x-ray source 108 emitting x-ray beam 109, and an x-ray imaging receptor housing 110, and can be moved up and down column 1000 to match patients of different heights, as in the embodiments described above. Shield 1004 shields the patient from the x-ray source 108 as it rotates around breast compression unit 104, and also shields the patient from any rotation of x-ray imaging receptor housing 110. Shield 1004 further acts to stabilize the patient leaning against it, and may include handles 1004e that the patient may hold to further facilitate patient comfort and stability. Shield 1004 can surround that rotational trajectory of source 108 and housing 110, and may include a front portion 1004b that has an opening for the patient's breast, which opening may be sufficiently large to allow a health professional to reach in to adjust the breast as it is being compressed. Shield 1004 may further include a breast platform that is between housing 110 and a portion of breast compression unit 104, on which the patient's breast may rest and be compressed by a paddle on the other side of the breast, particularly for the CT mode of operation but possibly in other modes as well. The breast platform can be flat, or it can be shaped to the contour of a breast (e.g., the platform can be concave), and can be made in different sizes that can be changed from one patient to another. An alternative shield 1004 can be used instead of or in addition to shield 1004. Shield 1004a surrounds compression unit 104 (104'), and preferably includes a portion 1004b that also protects the patient from motion of gantry 1006. Some or all of portion 1004*b* may be removable, particularly for taking mammograms M.

Figure 11:
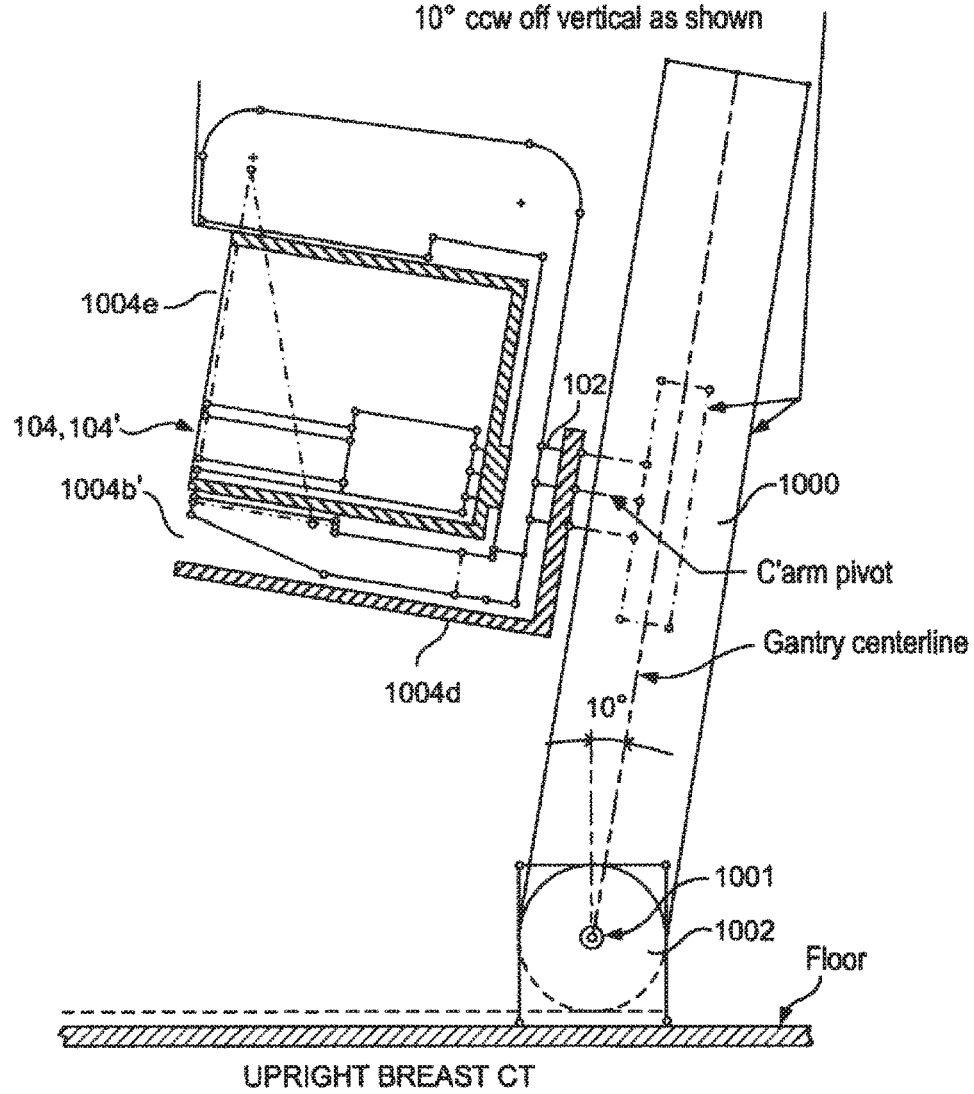

FIG. 11 illustrates another example, which is otherwise similar to that of FIG. 10 but has a differently shaped patient shield 1004*d*, which can be supported on axle 102, and can include a front portion 1004*b*' that is similar in position and function to portion 1004*b* in FIG. 10 but is somewhat differently shaped. As with shield 1004, shield 1004*d* can include a breast platform that is flat or shaped and can be in different sizes and can include patient handles. An alternative shield 1004*e* can be used in addition to or instead of shield 1004*d*, which has a different shape from shield 1004*a* but serves a similar purpose. The example of FIG. 12 allows greater freedom for positioning the patient's lower body relative to the x-ray system that shield 1004.

The above specific examples and embodiments are illustrative, and many variations can be introduced on these examples and embodiments without departing from the spirit of the disclosure. For example, elements and/or features of different illustrative embodiments described above may be combined with each other and/or substituted for each other within the scope of this disclosure.

Thus, this patent specification describes a multi-mode x-ray system for imaging a breast of an upright patient comprising: a breast immobilization unit configured to immobilize a breast of an upright patient; an x-ray source on one side of a patient's breast immobilized in said unit and an x-ray imaging receptor on the other side of the breast, said source selectively emitting an imaging beam of x-rays and said receptor receiving said imaging beam, and said source and receptor being mounted for selective movement about the breast; an x-ray data acquisition unit coupled with said source and receptor and configured to selectively operate said system in a CT mode in which the source and receptor move about the immobilized breast of the upright patient through a CT angle of at least 180° and the receptor generates image data for a plurality of projection images CTp of the breast taken at different angles within said CT angle; an image processing unit configured to receive and computer-process at least some of said image data for said images CTp to thereby generate reconstructed images CTr representing slices of the breast having selected thicknesses and orientations, and to produce display slice images CTrd based thereon; and a display unit receiving said selectively displaying said display images CTrd for viewing.

The x-ray data acquisition unit can be further configured to selectively operate the system in a tomosynthesis mode T rather than in the CT mode, in which mode T the source traverses angular positions relative to the breast through a tomosynthesis angle T that is less than 180° and the receptor generates tomosynthesis projection images Tp of the breast taken at different angular positions of the source within said angle T; the image processing unit can be further configured to receive and computer-process at least some of the image data for images Tp to thereby generate reconstructed images Tr representing slices of the breast having selected thicknesses and orientations, and to produce display slice images Trd and display projection images Tpd based on the image data for the images Tp; the display unit can be further configured to selectively display said display images Tpd, Trd and CTrd; and the data acquisition and display units being further configured to select the CT mode or the tomosynthesis mode for operation.

The tomosynthesis mode can comprise a narrow-angle tomosynthesis mode Tn and a wide-angle tomosynthesis mode Tw, wherein: the x-ray data acquisition unit is further configured to selectively operate (i) in the mode T by causing at least the source to traverse angular positions relative to the breast through a relatively narrow angle and to cause the receptor to generate tomosynthesis projection images Tpn of the breast taken at different angular positions within the narrow angle, and (ii) in the mode Tw by causing at least the source to traverse angular positions relative to the breast through a relatively wide angle, wider than the narrow angle, and to cause the receptor to generate tomosynthesis projection images Tpw of the breast taken at different angular positions of the source within the angle Tw; the image processing unit is further configured to receive and computer-process at least some of the image data for images Tpn and Tpw to thereby generate reconstructed images Tr representing slices of the breast having selected thicknesses and orientations, and to produce display slice images Trd and display projection images Tpnd and/or Tpwd based on the image data for projection images Tpn and/or Tpw; the display unit is further configured to selectively display the display images Tpnd, Tpwd, Trd and CTrd; and the data acquisition and display units are further configured to select a mode of operation among the CT, Tn and Tw modes.

The x-ray data acquisition unit can be further configured to selectively operate the system in a mammography mode M, rather than in the CT mode or the tomosynthesis mode T, to thereby generate M image data for one or more projection mammograms Mp, each at a higher patient x-ray dose than a single one of the images Tp; the image processing unit can be further configured to receive and computer-process at least some of the image data for the one of more images Mp to thereby generate one or more display mammogram image Mpd; the display unit can be further configured to selectively display the display images Tpd, Trd, CTrd and Mpd; and the data acquisition and display units being further configured to select the CT, T or M mode of operation.

The data acquisition unit can be configured to vary the hardness of the imaging beam of x-rays with movement of the source relative to the breast at least in one of the CT and T modes of operation.

The breast immobilization unit can comprise an upper plate and a lower plate facing each other, wherein the facing portions of the plates are concave where engaging the breast for immobilizing the breast.

The display unit can be configured to concurrently display at least one of the images CTrd and at least one of the images Tpd and Trd in co-registration such that the selection of an anatomical feature in one of the concurrently displayed images automatically identifies a matching anatomical feature in at least another one of the concurrently displayed images.

The data acquisition unit includes a shield separating the patient from the moving source and x-ray receptor in each of said modes of operation while permitting the breast to remain immobilized between the platform and paddle.

In another preferred embodiment, an x-ray system for imaging a compressed breast of a patient with x-rays comprises: a breast immobilization unit configured to compress a patient's breast; an x-ray source on one side of the immobilization unit and an x-ray imaging receptor on the other side, mounted for movement about a breast compressed in said unit, x-ray data acquisition unit coupled with the source and receptor and configured to operate the system in a CT mode in which the source and receptor move about the breast through an angle of at least 180°, and the x-ray receptor generates image data for a plurality of projection images CTp of the breast; an image processing unit configured to receive and computer-process at least some of the image data for the images CTp and computer-process the received data to generate reconstructed CT images CTr representing slices of the breast having selected thicknesses and orientations, and to produce display slice images CTrd based thereon; and a display unit receiving and selectively displaying the display images CTrd for viewing.

The immobilization unit can be configured to compress the breast of an upright patient.

The compressed breast can have a dimension in a first direction that is substantially less than in a second direction that is transverse to the first direction, and the data acquisition unit can be configured to vary the hardness of the imaging beam of x-rays with movement of the source relative to the breast so that the x-ray beam is harder when the x-rays are closer to the second direction than to the first direction.

The x-ray source can comprise an x-ray tube and the data acquisition system can be configured to vary the hardness of the imaging beam by varying a selected characteristic of electrical power driving the x-ray tube. The selected characteristic can be a voltage (kV) of the power driving the x-ray tube.

In yet another preferred embodiment, the disclosed invention can be an x-ray system for imaging a patient's breast comprising: an upper an a lower plates facing each other and configured to immobilize a patient's breast; each of said plates having a breast-engaging surface that is concave where engaging the compressed breast; an x-ray source on one side of said plates, and an x-ray imaging receptor on the other side, wherein at least said source is mounted for movement about the breast; a data acquisition unit coupled with the source and receptor and configured to cause the source to selectively generate an imaging x-ray beam at each of a plurality of angles of the source relative to the breast and to cause the receptor to generates image data for a plurality of projection x-ray images of the breast; an image processing unit configured to receive and computer-process at least some of the received data to generate display images of the breast; and a display unit receiving said selectively displaying said display images for viewing. In this system, the data acquisition unit can be further configured to cause the x-ray beam to have an x-ray hardness that varies depending on the angle of said beam relative to the breast.

Yet another embodiment is a multi-mode x-ray tomosynthesis system for imaging a patient's breast comprising: a breast immobilization unit configured to immobilize a patient's breast; an x-ray source on one side of the immobilization unit and an x-ray imaging receptor on the other side; at least the x-ray source being mounted for movement about the immobilized breast; an x-ray data acquisition unit coupled with the source and receptor and configured to operate the system selectively in (i) a pre-set narrow angle tomosynthesis mode Tn, and (ii) a pre-set wide angle tomosynthesis mode Tw, wherein (a) in the Tn mode at least the source traverses angular positions relative to the breast through a relatively narrow angle Tn and the receptor generates image data for tomosynthesis projection x-ray images Tpn of the breast within said angle Tn, and (b) in the Tw mode at least the source traverses angular positions relative to the breast through a relatively wide angle Tw and the receptor generates image data for a second plurality of tomosynthesis projection x-ray images Tpw of the breast within the angle Tw; an image processing unit configured to receive and computer-process at least some of the image data for the images Tpn and Tpw to selectively generate display images of (i) at least some of said images Tpn and Tpw and (ii) reconstructed tomosynthesis images Tr derived from image data for at least some of the images Tpn and Tpw and representing slices of the breast of selected thicknesses and orientations; and a display system selectively displaying sets of one or more of said display images for viewing; wherein the data acquisition and display units are further configured to select a Tn or Tw mode of operation.

Yet another embodiment is a multi-mode x-ray system for imaging a patient's breast comprising: a breast immobilization unit configured to immobilize a patient's breast; an x-ray source on one side of the immobilization unit and an x-ray imaging receptor on the other side, mounted for movement about the immobilized breast; an x-ray data acquisition unit coupled with the source and receptor and configured to operate said system selectively in (i) a narrow angle tomosynthesis mode Tn, (ii) a wide angle tomosynthesis mode Tw, (iii) a computerized tomography (CT) mode, and (iv) a mammography mode M, wherein: (a) in the Tn mode at least the source traverses a first plurality of angular positions relative to the breast through a relatively narrow angle and the receptor generates image data for a first plurality of tomosynthesis projection x-ray images Tpn of the breast, (b) in the Tw mode at least the source traverses a second plurality of angular positions relative to the breast through a relatively wide angle and the receptor generates image data for a second plurality of tomosynthesis projection x-ray images Tpw of the breast; and (c) in the CT mode, the source and the receptor rotate about a length of the breast through an angle greater than said wide angle, and the receptor generates image data for a third plurality of projection images CTp of the breast, wherein the images CTp are greater in number than the images in each of the pluralities of images Tpn and Tpw, and (d) in the M mode the source and the receptor generate one or more projection images Mp of the breast, using for each of said images Mp a patient x-ray dose greater than for any one of the images Tpn and Tpw; an image processing unit configured to receive at least some of said image data and computer-process the received data to generate display images of at least some of (i) said projection images Tpn and/or Tpw, (ii) reconstructed tomosynthesis images Tr derived from image data for at least some of said projection images Tpn and/or Tpw and representing slices of the breast having selected thicknesses and orientations, (iii) reconstructed CT images CTr representing slices of the breast having selected thicknesses and orientations, and (iv) one or more mammograms Mp representing projection images of the breast; and a display system selectively displaying sets of one or more of said display images for viewing.

Yet another embodiment is a multi-mode x-ray system for imaging a patient's breast comprising: a breast immobilization unit configured to immobilize a patient's breast; an x-ray source on one side of the immobilization unit and an x-ray imaging receptor on the other side, mounted for movement about the immobilized breast; a x-ray data acquisition unit coupled with said source and receptor and configured to operate said system to generate image data for projection images taken at different angles of at least the x-ray source relative to the breast; an image processing unit configured to receive at least some of said image data and to computer-process the received data to generate CT slice images of the breast representing slices of the breast having selected thicknesses and orientation and to further generate at least some of (i) tomosynthesis projection images Tp, and (ii) tomosynthesis slice images Tr reconstructed from at least some of the image data for said images Tp and representing slices of the breast having selected thicknesses and orientations; and a display system selectively displaying at least one or more of said CT images said Tp and Tr images for viewing.

Yet another embodiment is an x-ray system for imaging a breast of a patient comprising: an x-ray source and an x-ray imaging receptor mounted for movement about a position for a patient's breast such that an imaging x-ray beam impinges on the receptor after passing through the breast; an x-ray data acquisition unit coupled to the source and the receptor and configured to cause at least the source to move to different angular positions relative to the breast and emit an imaging x-ray beam at each angular position and to cause the receptor to generate image data for projection images taken at said angular positions; said data acquisition unit being further configured to cause the x-ray hardness of said imaging x-ray beam to vary with movement of the source from one a said angular positions to another; an image processing unit configured to receive at least some of said image data and computer-process the received data to generate display images of the breast derived from said projection images; and a display system receiving said selectively displaying said display images for viewing.

Yet another embodiment is a system for acquiring and displaying for concurrent viewing co-registered x-ray CT images and other x-ray images of a patient's breast comprising: a source of x-ray image data describing (1) CT slice images representing first slices of a patient's breast and (ii) non-CT x-ray images of the breast; an image processing unit configured to receive at least some of said image data and generate therefrom (i) display CT images of slices of the breast and (ii) non-CT display images of the breast; and a a display unit configured to display for concurrent viewing at least one of said display CT images and at least one of said non-CT display images; said display unit being further configured to cause said concurrently displayed images to be co-registered such that a mark placed by the system or user at an anatomical feature on one of the displayed images automatically appears at a matching anatomical feature of at least one other concurrently displayed image.

An embodiment of a method of breast imaging according to the disclosure above comprises: compressing a breast of an upright patient between a an upper plate and a lower plate; providing an x-ray source on one side of said plates and an x-ray imaging receptor on the other side; selectively imaging the patient's compressed breast with x-rays from: the x-ray source received at the x-ray receptor after passage through the breast in: (a) a narrow angle tomosynthesis mode generating a plurality of tomosynthesis projection x-ray images Tpn of the compressed breast taken over a relatively narrow extent of respective different angles of the x-ray source relative to the breast, (b) a wide angle tomosynthesis mode generating a plurality of tomosynthesis projection images Tpw of the compressed breast taken at a relatively wider extent of respective different angles of the x-ray source relative to the breast, (c) a computerized tomography (CT) mode generating a plurality of CT images of the compressed breast taken while the x-ray source and the x-ray imaging move around the breast over an angle greater than said relatively wider extent, and (d) a mammography mode generating one or more projection images Mp of the compressed breast, each using a patient dose approximating that for a conventional mammogram; selectively moving the x-ray source and the x-ray imaging receptor in a direction generally along a length of the compressed breast from a position for one of said modes to a position for another of said modes; varying the x-ray source kV with the angle of the x-ray source relative to the breast while taking said images Tpw and/or said CT images; selectively computer-processing said images Tpn and Tpw to produce reconstructed tomosynthesis images Tr of selected slices of said breast; and displaying selected combinations of one or more of said Tpn, Tpw, Tr and CT images for concurrent viewing.

The invention claimed is:

1. A system for imaging a breast of an upright patient with x-rays comprising:
a breast compression unit configured to at least partially compress a breast of an upright patient between a pair of compression surfaces;
an x-ray data acquisition unit configured to operate the system in:
a computerized tomography (CT) mode to thereby generate a plurality of CT x-ray projection images CTp of the breast taken at different angles to the breast; and
a tomosynthesis mode T to thereby generate a plurality of tomosynthesis x-ray projection images Tp of the breast taken at different angles to the breast; and
an image processing unit configured to computer-process the images CTp to thereby generate a reconstructed image CTr and to computer process the images Tp to thereby generate tomosynthesis reconstructed breast slice images Tr of at least a portion of the breast.

2. The system of claim 1, further including a patient shield secured to the system and forming a barrier between the upright patient and moving elements of the system when operating in the CT mode.

3. The system of claim 2, in which the patient shield is configured to tilt to an inclined position in which the upright patient can lean forward against the shield.

4. The system of claim 2, in which the shield includes handles for the patient to hold to facilitate comfort and stability while the patient's breast is being imaged.

5. The system of claim 1, in which the x-ray data acquisition comprises an x-ray source that is configured to rotate around the breast over a first angle for generating the projection images Tp and through a second angle that is greater than the first angle for generating the projection images CTp.

6. The system of claim 5, in which the second angle is at least 180 degrees.

7. The system of claim 1, in which the x-ray data acquisition unit is further configured to vary hardness of x-rays impinging on the breast with change in the angle at which the projection images CTp are taken.

8. The system of claim 1, in which the x-ray data acquisition unit is further configured to selectively operate the system in a mammography mode M to thereby generate one or more projection mammograms Mp, wherein each image Mp is taken at a higher patient x-ray dose than a single one of the images Tp.

9. The system of claim 1, further comprising a display unit configured to concurrently display at least one of the images CTr and at least one of the images Tp and Tr in co-registration such that the selection of an anatomical feature in one of the concurrently displayed images automatically identifies a matching anatomical feature in at least another one of the concurrently displayed images.

10. The system of claim 1, in which the x-ray data acquisition system comprises an x-ray source and an x-ray imaging receptor moving in a direction generally along a length of the breast from a position for one of said modes to a position for another of said modes.

11. The system of claim 1, in which the x-ray data acquisition unit is further configured to operate in said mode T by responding to an input to select between (i) a narrow angle mode Tn in which the projection images Tp are taken at angles over a relatively narrow angle Tn to thereby form a set of images Tpn of the breast, and (ii) a wide angle mode Tw in which the projection images Tp are taken over an angle Tw that is wider than Tn to thereby form a set of images Tpw of the breast.

12. A system for imaging a breast of an upright patient with x-rays comprising:
   a breast compression unit configured to at least partially compress a breast of an upright patient;
   an x-ray data acquisition unit comprising an x-ray source emitting an imaging x-ray beam toward an x-ray imaging receptor and configured to operate the system in a computerized tomography (CT) mode to take CT x-ray projection images CTp of the upright patient's breast taken at different angles of the imaging x-ray beam to the breast;
   a support for the x-ray tube and the x-ray receptor configured to tilt to a position in which the imaging x-ray beam is tilted away from the vertical, causing the patient to lean into the data acquisition unit for imaging the patient's breast while remaining generally upright.

13. The system of claim 12, in which said x-ray data acquisition unit is further configured to operate in a tomosynthesis mode T to take tomosynthesis x-ray projection images Tp of the breast taken at different angles of said imaging x-ray beam to the breast.

14. The system of claim 12, further comprising a reconstruction unit configured to reconstruct images CTr of the breast from the CTp images and images Tr from the images Tp, and a display unit configured to concurrently display at least one of the images CTr and at least one of the images Tp and Tr in co-registration such that the selection of an anatomical feature in one of the concurrently displayed images automatically identifies a matching anatomical feature in at least another one of the concurrently displayed images.

15. The system of claim 12, further including a patient shield secured to the system and forming a barrier between the upright patient and moving elements of the system when operating in the CT mode.

16. The system of claim 15, in which the shield includes handles for the patient to hold to facilitate comfort and stability while the patient's breast is being imaged.

17. The system of claim 12, in which the x-ray data acquisition system further comprises handles for the patient to hold to facilitate comfort and stability while the patient's breast is being imaged.

18. The system of claim 12, in which the x-ray data acquisition system is configured to vary hardness of the imaging x-ray beam with the angle at which the projection images CTp are taken.

19. A method of imaging a breast of an upright patient with an x-rays system comprising:
   at least partially compressing the breast into a non-circular cross-section;
   responding to a selection signal to image the breast with x-rays either in either one or in both of the following modes:
      (a) a computerized tomography (CT) mode generating a plurality of two-dimensional projection x-ray images CTp of the breast taken at respective CT angles of an imaging x-ray beam to the breast; and
      (b) a tomosynthesis mode T generating a plurality of two-dimensional tomosynthesis projection x-ray images Tp of the breast taken at respective tomosynthesis angles of the imaging x-ray beam to the breast;
   reconstructing images CTr of the breast from said images CTp and slice tomosynthesis images Tr of the breast from said images Tp; and
   displaying selected combinations of two or more of said CTr, Tp, and Tr images for concurrent viewing in co-registration.

20. The method of claim 19, further comprising tilting the imaging x-ray beam to a tilted position in which the upright patient leans away from a vertical position.

* * * * *